United States Patent [19]
Lehmann et al.

[11] Patent Number: 4,781,685
[45] Date of Patent: Nov. 1, 1988

[54] IMPLANTABLE DRUG-DISPENSING CAPSULE AND SYSTEM FACILITATING ITS USE

[75] Inventors: Gérard Lehmann, Neuville de Poitou; Joël Metais, Monts Sur Guesnes; Jean-François Meunier, Noisy le Grand; Jean-Philippe Gautier, Ozoir la Ferriere, all of France

[73] Assignees: Celsa Composants Electriques, Monts Sur Guesnes; R. D. M. Medical, Brie Comte Robert, both of France

[21] Appl. No.: 36,228

[22] Filed: Apr. 9, 1987

[30] Foreign Application Priority Data

Apr. 16, 1986 [FR] France .............................. 86 05462
Apr. 6, 1987 [EP] European Pat. Off. ....... 87 400759.4

[51] Int. Cl.⁴ .............................................. A61M 5/00
[52] U.S. Cl. .................................... 604/117; 128/734; 604/175
[58] Field of Search ............... 128/734, 630; 604/175, 604/117

[56] References Cited

U.S. PATENT DOCUMENTS

| | | | |
|---|---|---|---|
| 3,951,147 | 4/1976 | Tucker et al. | 222/386.5 |
| 3,993,044 | 11/1976 | McGuffin | 32/57 X |
| 4,273,531 | 6/1981 | Hasegawa | 128/734 X |
| 4,356,826 | 11/1982 | Kubota | 604/117 X |

FOREIGN PATENT DOCUMENTS 2922239 12/1980 Fed. Rep. of Germany ...... 604/117
83/02063 6/1983 World Int. Prop. O. .

*Primary Examiner*—William E. Wayner
*Attorney, Agent, or Firm*—Pollock, VandeSande & Priddy

[57] ABSTRACT

The invention concerns an implantable drug-dispensing capsule and a process and system facilitating its use. According to the invention, a mechanism (7) for detecting the proximity of the injection needle (1) is provided inside the body (5) of the capsule (3), which detection mechanism is connected to an external signaling device (32) which signals when this proximity is realized.

The invention is in particular applicable to the injection of various drugs in localized sites.

8 Claims, 2 Drawing Sheets

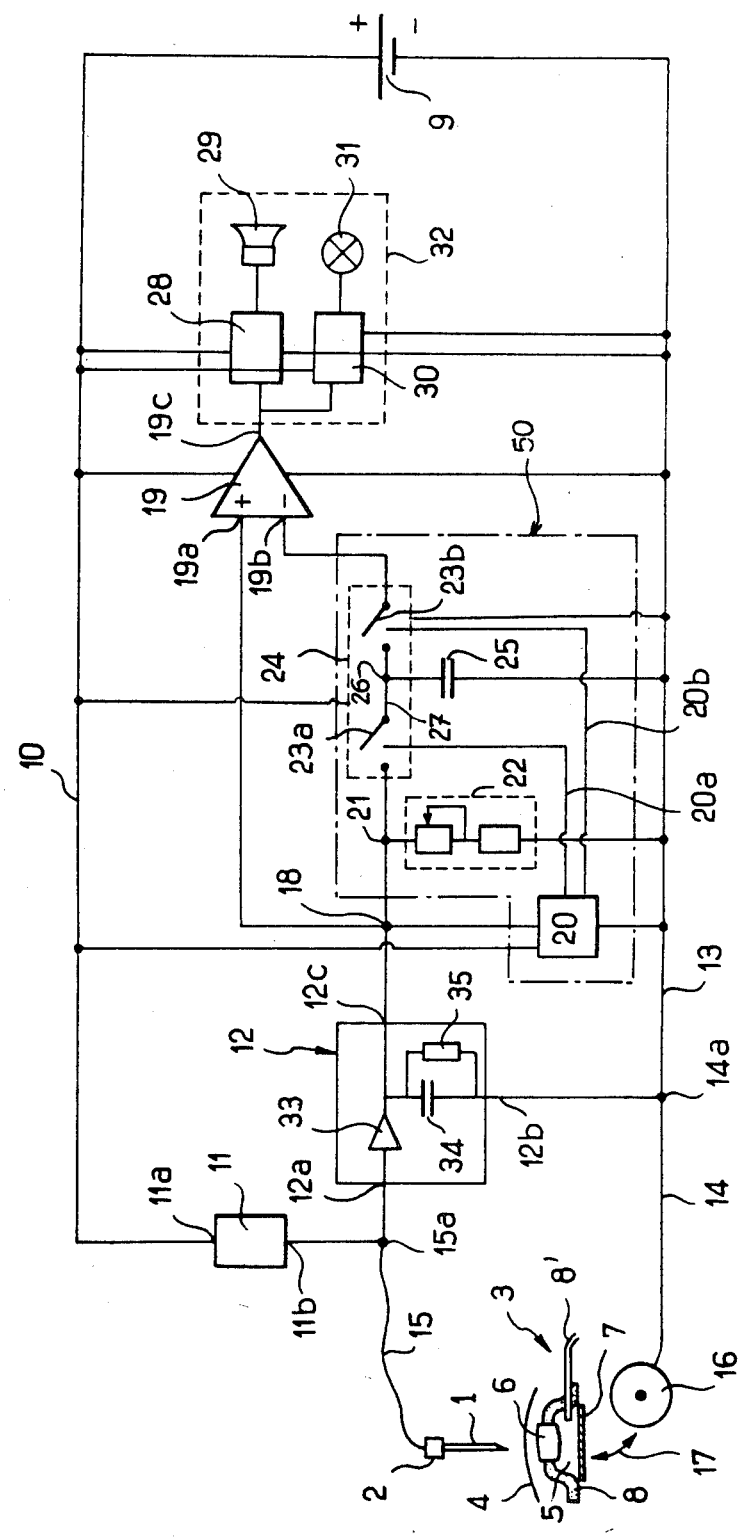
FIG_1

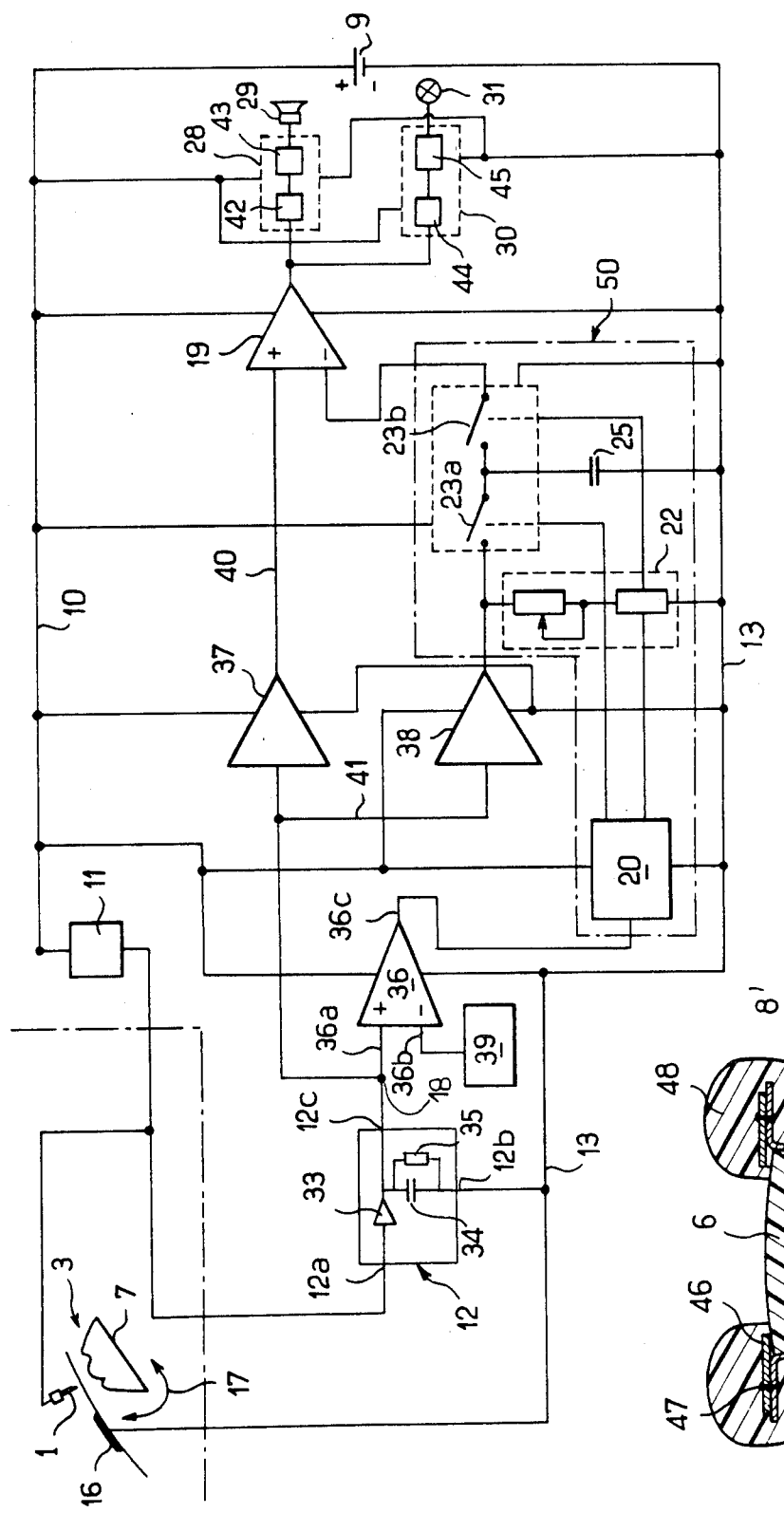
FIG._2
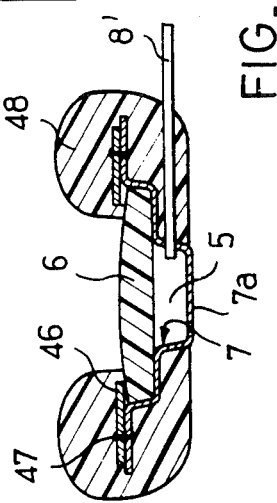
FIG._3

4,781,685

IMPLANTABLE DRUG-DISPENSING CAPSULE AND SYSTEM FACILITATING ITS USE

FIELD OF THE INVENTION

The invention concerns a device facilitating the use of an implantable drug-dispensing capsule.

BACKGROUND OF THE INVENTION

In treating certain serious diseases, frequent injections of various drugs are required. Often these injections must be given venously or arterially, or by other means, so as to ensure local and precise distribution of the drugs used in treatment. In order to avoid inserting and withdrawing a catheter when each injection is administered, for many years now recourse has been had to implantable drug-dispensing capsules, placed under the patient's skin at a suitable point, and whose inner body communicates with a tube left in place in the body and emerging at the point where the injections are to be given. The capsule has a perforatable wall through which it is possible to inject the drug to be dispensed by means of a needle, the wall closing up again automatically when the needle is withdrawn.

Generally speaking, and as it is understood in this field of application, a serious, fundamental problem presents itself with regard to the assurance that must be given to the practitioner that the needle is correctly introduced into the inner body of the dispensing capsule. Indeed, some of the drugs used may be of doubtful efficacy and cause the patient's death, or serious mishaps, if the drug injection, by mistake, is not made inside the body of the capsule and spreads, for example, between the capsule and the skin covering it.

In some systems for registering the proper introduction of the needle of the injection syringe into the body of the drug-dispensing capsule, this same capsule is placed in contact by its outer wall with the patient's body and has an electrically conducting inner wall forming a detection device near the end of this needle. In addition, it is known that the registering system can be equipped with an external signaling apparatus, connected to the aforementioned detection device, which responds to the closing through the patient's body of an electrical circuit that includes the inner conducting wall of the aforementioned capsule and the needle.

Such systems nonetheless present a certain number of drawbacks.

Indeed, it has been recognized that, together with the fundamental problem regarding assurance of proper introduction of the needle, practical difficulties were posed for the application and utilization of the known systems. More precisely, it was noted that the signaling device that alerts the practitioner to the correct introduction of the needle was sometimes prematurely triggered while the needle was still not in contact with the bottom of the capsule. A slight variation in impedance, too rapid, could trip the device, understandably posing a real danger to the patient.

BRIEF DESCRIPTION OF THE PRESENT INVENTION

The invention is particularly intended to solve this difficulty, together with the fundamental problem mentioned previously, by enabling the practitioner to determine with certainty the moment when the injection needle is actually and correctly introduced up to the inner conducting wall inside the body of the capsule, without the risk of premature, too rapid tripping of the signaling device informing him that he may inject the drug.

This purpose is achieved according to the invention by providing that the electrical circuit of the aforementioned registering system includes, in addition to the capsule's inner conducting wall and the needle, an AC generator, the lead-in of which is connected to the positive pole of a DC voltage source,
an assembly of the rectifier/filter type, said assembly being connected:
    by a first input terminal, to the outlet of the aforesaid AC generator,
    by a second terminal, to the negative pole of said DC source,
at least one comparator connected
    by lead-out, to said signaling device,
    by lead-in, to a third output terminal of the rectifier/filter assembly and to a comparison unit intended to provide a reference voltage, said comparator being subjected to the difference in voltage between that delivered by said rectifier/filter assembly and that delivered by said comparison unit, and being fed, along with said signaling device, by said DC source,
a surface electrode placed on the patient's skin, said electrode being connected in the circuit's closed state in series with said needle, the patient's body, and/or said inner wall of the capsule towards the input terminal of said rectifier/filter assembly.

According to a preferred characteristic, the aforementioned comparison unit includes:
a sequencing clock, one input terminal of which is connected to the output terminal of the rectifier/filter assembly,
two switches placed on the clock's control,
a condenser or similar device that discharges towards an input of the comparator in a closed position of one of the switches, and
a voltage-dividing bridge charging the condenser in the closed position of the other switch, the two switches working in anti-parallel phases.

In this way, the system is prevented from taking into account small variations in impedance, the magnitude of which is basically a function of the speed at which the injection needle is introduced.

In other words, this invention ensures that the signaling device is tripped only when the impedance drops suddenly and relatively significantly, i.e., basically only upon contact between the end of the injection needle and the inner conducting wall of the capsule.

It will likewise be noted that the invention, by providing an AC generator, makes it possible to solve a delicate problem regarding the overall effectiveness of the system. Indeed, by the capsule being placed under the skin and being utilized, fibrous tissues are created around the capsule which hinder the passage of electrical energy, especially that which would be delivered by a DC generator or source. Operation on AC solves this additional difficulty.

In addition, such a current generator is entirely suitable in that it makes it possible to control the electrical energy passing through the patient's body by checking only one variable: the current.

The invention and its implementation will appear more clearly with the aid of the following description, given in reference to the attached drawings illustrating methods of implementation. In these drawings:

BRIEF DESCRIPTION OF THE FIGURES

FIG. 1 is a synoptic diagram of an assembly that can be utilized according to the invention, FIG. 2 illustrates a somewhat more complete assembly than the one in FIG. 1, and FIG. 3 shows in cross-section a dispensing capsule usable according to the invention.

DETAILED DESCRIPTION OF THE INVENTION

It will immediately be noted that, in FIGS. 1 and 2, the circuit's linkage or nodal points have been marked by a dark dot in order to facilitate reading the drawings.

Referring first to FIG. 1, the needle 1 has been shown with its head 2 for adapting it to any appropriate injection and/or puncture system (not shown). Opposite is shown a capsule 3 implantable under a patient's skin 4, this capsule including a self-sealing wall 6, enclosing its inner body 5, of a type that is known, especially in silicone-coated plastic. The bottom inner wall 7 of the capsule is metal, whereas the rest of the capsule, and particularly the side wall 8, is of an electrical insulating material, such as a plastic of a suitable quality. The capsule's body 5 communicates with a tube 8' through which are injected the drugs to be introduced, and through which drawoffs for analyses or punctures can also be made. The invention's system also includes a DC source 9 of a suitable quality (voltage/density). According to the invention, the input 11a of an AC generator 11 is connected to the positive pole of the DC source 9 through a feed line 10. The output 11b of this same generator 11 is connected to an input terminal 12a of an assembly 12 forming a rectifier/filter.

The assembly 12 includes, as illustrated, a diode 33, or similar device, forming a rectifier connected between the input 12a and the output 12c, a condenser 34 connected on one side to the unit's feed line, towards the diode's cathode, and on the other, leading out from the terminal 12b, to the negative pole of the source 9, through the circuit's ground line 13. Parallel to the condenser's terminals is mounted a relatively strong resistor 35.

The diode is mounted passing towards the assembly's output 12c.

At 17, the double arrow indicates the reduced-resistance electrical path existing through the patient's body between a surface electrode 16 connected at 14a by a conductor 14 to the ground line 13 and the relatively broad-surfaced metal wall 7 of the capsule 3. A conductor 15 also makes it possible to connect at 15a the head 2 of the needle 1 between the output 11b of the AC generator 11 and the input terminal 12a of the assembly 12. Thus, when the needle 1 comes into contact with at least the patient's skin 4, the circuit is closed in series over the needle, the surface electrode, and the patient's body.

Connected to the output terminal 12c of the aforementioned rectifier/filter unit 12 are, at the site of a node 18, the positive input 19a of a comparator 19, itself connected to the signaling device 32, and a comparison unit 50 intended to supply to the negative input 19b of this same comparator a variable voltage, as will be seen subsequently. The unit 50 includes a clock 20, a voltage divider 22, a condenser 25, and two switches 23a, 23b. The input terminal of the sequencing clock 20 is connected to the node 18, while one of the poles of the voltage divider 22 is connected at 21, also to the terminal 12c of the assembly 12. The other pole of this same divider is linked with the ground line 13.

The two switches 23a, 23b are placed under the dependency of the clock 20. They are connected on the one hand to one another by means of a conductor 27, and, on the other, at the site of their respective remaining terminal, for the assembly 23a, to the lead-out line of the switch 12, at 21, and, for the switch 23b, to the negative input 19b of the comparator 19.

Connected at 26 to the conductor 27 of one terminal of each of the two switches is one pole of the condenser 25, the other pole of which is connected to the ground line 13.

In the case envisaged, the switches are of the "all or nothing" type, open or closed. In the figures, they have both been represented in the open position, even though they are intended to operate in anti-parallel phase.

The drive or control action of the clock 20 on the two switches 23a, 23b is achieved through two conductors respectively 20a, 20b connected to two output terminals of the clock 20.

With regard to the signaling device 32, it will be noted, as illustrated, that the output 19c of the comparator 19 is parallel-connected both to a device 28 for shaping a sound signal that will be able to activate a sound device 29 and to a device 30 for shaping the signal that will be able to activate a signal light 31.

In order to ensure operation of the circuit just described, the DC source 9, which may in particular be a simple galvanic cell, shunt-feeds, through the feed line 10 and the ground line 13, the two signal-shaping devices 28, 30, the comparator 19, the unit 24 including the two switches 23a, 23b, and the sequencing clock 20.

The operation of the invention's system, the assembly circuit of which has just been described, can be clearly deduced from the foregoing.

In the state illustrated in the figure, where the needle 1 is drawn back from the metal conducting wall 7 of the capsule 3, the electrical circuit through the needle and the capsule is open, there being a virtually infinite resistance between its terminals.

When the needle 1 is pushed through the patient's skin 4, resistance decreases, the electrical circuit being closed through the patient's body and skin. However, this resistance is still very strong because of the limited, pinpoint contact between the needle 1 and the skin 4 at the site where this same needle is passing through the skin. By way of example, it will be noted that this resistance may be on the order of 30,000 ohms.

Finally, when the needle has perforated the wall 6 and comes in contact with the metal wall 7 of the capsule, the resistance decreases considerably, not exceeding 1,000 ohms, for example. At the site of the comparator 19, it is this variation in impedance which is exploited by the comparator to trip the signals.

Of course, the system is time-delayed so that the sound signal and the light signal last long enough to eliminate any doubt from the user's mind that the signal is present.

In fact, the comparator will only trigger the signals if the voltage reaching its positive terminal 19a is lower than a previously memorized voltage reaching its negative terminal 19b.

Indeed, once the circuit is closed and the source 9 receives voltage, the clock is triggered and alternately controls the switch 23a or the switch 23b at each surge.

At the same time, the AC generator 11 feeds the assembly 12 (diode 33, condenser 34, resistor 35) which receives, at 12a, an alternating current, rectifies it, filters it, or integrates it, and puts out between its terminals 12c, 12b a direct current U as a function of the current passing through the resistance of the patient's body and/or in the capsule. The voltage U occurs again at the terminals of the voltage divider 22 and at the positive input 19a of the comparator 19.

Let $p$ be the surge phase of the clock which, upon closing, controls the switch 23a, and $\overline{p}$ the phase which, also upon closing, controls the switch 23b. It will be recalled that the two switches work, preferably, in anti-parallel phases.

In phase $\overline{p}$, the switch 23a is closed, while 23b is open. The condenser 25 is charged by the voltage delivered by the voltage divider 22, i.e., by a fraction of the voltage U, or U/X with X: the ratio of the voltage divider.

In phase $p$, the switch 23b is closed, while 23a is open. The condenser 25 then discharges towards the negative input 19b of the comparator 19, which then compares the value of a voltage U' which has just been received at its positive terminal 19a to the memorized voltage value U/X received at its negative terminal 19b. In other words, the comparator 19 makes a comparison between a voltage proportional to the current that has just passed through the patient's body and a previous fractional value of that voltage which was stored in the condenser.

In particular, it is possible to see that the voltage divider 22 is set with X=4. The voltage delivered will then be U/4, with a voltage U at the input.

The comparator 19 will then trigger the signals if it receives a voltage U' lower than U/4, i.e., if there is a significant collapse in impedance indicating contact between the needle 1 and wall 7 of the capsule, and hence a correct introduction of the needle.

The clock 20 can be set at about 100 times the speed $v$ of the needle's penetration into the site. It is possible to take $v$ on the order of 100 ms, and, hence, $p(or \overline{p})$ equal to about 1 ms. The needle's speed of introduction is thus prevented from interfering with the operation of the system and causing a premature tripping of the signals.

Reference will now be had to FIG. 2, in order to see illustrated a preferred and somewhat more complete mode of realization of the electrical assembly represented in FIG. 1.

The circuit in FIG. 2 includes all components presented in reference to FIG. 1 and which have consequently been assigned the same numbers and will not be described again.

In particular, in addition to the needle, also present once again are the capsule 3 and the surface electrode 16, the AC generator 11, the rectifier/filter assembly 12, the clock 20, the voltage divider 22, the switches 23a and 23b, the comparator 19 and the signaling device 32, as well as the DC source 9.

A second comparator 36 and two voltage followers respectively 37 and 38 have been added to the assembly.

In addition, the signal-shaping devices 28, 30 have been illustrated in greater detail.

More specifically, the second comparator 36 has been placed between the node 18 and the input terminal of the clock 20. More precisely, its positive input pole 36a is linked to the output terminal 12c of the rectifier/filter assembly 12, while its negative input pole 36b is connected to a comparison or reference unit 39, known in itself, delivering a fixed voltage.

The comparator 36 is set so that it controls the triggering of the clock 20 when the voltage applied to its pole 36a falls below a determined threshold selected in relation to the voltage prevailing at its pole 36b which receives the reference voltage. In practice, the comparator will preferably be set to be triggered upon contact of the needle 1 with the patient's skin 4. It improves the system's reliability.

As for the voltage followers 37 and 38, they are respectively mounted on the feed line 40 of the positive terminal of the comparator 19 and on that 41 of the voltage divider 22, so that their respective inputs are subjected to the voltage U (or U') delivered by the rectifier/filter assembly 12.

With regard to the shaping devices 28, 30, each includes a monostable circuit 42, 44 controlled by the comparator 19 and, in series, an adaptation circuit 43, 45.

Of course, the comparator 36, the two followers 37, 38 and the components of the devices 28, 30 are shunt-fed by the DC source 9.

In terms of practical utilization, it will be noted that the model LD 161 manufactured by INTERSIL can be used as comparator 36. This same model would also be suitable for the comparator 19.

The two voltage followers 37, 38 could be of the TL081 type manufactured by TEXAS INSTRUMENTS.

In terms of selection of components, one could choose a condenser 25 of about 100 nF, a condenser 34 of about 10 nF, a resistor 35 basically equal to 2MΩ, an AC generator 11 delivering about about 100 μA with a current source 9 of about ±9V.

FIG. 3 will now be discussed; it illustrates the realization of a capsule specially adapted for the use described above.

The capsule basically includes a pressed-metal wall 7, of stainless steel or titanium, for example. The metal bottom has the shape shown in FIG. 3 of a basin, the inner body 5 of the capsule being enclosed by the self-sealing perforatable wall 6 placed on the basin. The wall 6 can be held in place by a metal washer 46 soldered as indicated at 47 towards the outer edge of the basin-shaped wall 7. The whole is then covered by a molded plastic material 48 electrically insulating the whole of the capsule from the patient's body, except for the bottom-center wall 7a of the capsule which will come in contact with the patient's body, a bone, for example, onto which the capsule will be fixed. Finally, the inner body 5 of the capsule communicates through a metal tube 8', appropriately soldered or crimped, passing through the wall 7, the assembly being suitably protected by the molded plastic 48. It will be noted that, with such a capsule, when the wall 6 is perforated by the injection needle, there is no risk of obtaining a false contact signal if the needle is poorly guided and runs into the insulating wall of the capsule's covering 48.

Several variants can be introduced in the modes of realization described, both in the constitution of the capsule and in the generation of the signal indicating correct and complete introduction of the needle into the body of the capsule as far as its inner metal bottom. For example, in the case of the assembly illustrated in FIG. 1, one might consider using, instead of the comparator 19 and the comparison unit 50, the aforementioned comparator 36 with its comparison unit 39.

In this case, the signaling device 32 would be connected directly to the output of the comparator 36. The remainder of the circuit would be identical to the one illustrated.

With such an assembly, and as it is understood, the variation in impedance associated with the needle's penetration towards the capsule's conducting bottom would be exploited by the comparator 36 to trigger at a determined threshold, for example 2,000 ohms, the signals indicating proper introduction. However, in this case there would of course be no comparison between an immediate voltage and a previous value that would have been stored for a short time. In other words, and in practice, such a system, though quite usable, would not make it possible to be free from the uncertainties of premature triggering of the signaling device associated with the needle's speed of penetration.

What is claimed is:

1. A system for registering proper introduction of an injection syringe needle into the body of a drug-dispensing capsule implantable under the skin of a patient, said capsule, placed in contact by its outer wall with the patient's body, including an electrically conducting inner wall forming a mechanism for detecting the proximity of the tip of said needle, and said system being equipped with an external signaling device connected to said inner wall and responding to the state of closure through the patient's body of an electrical circuit including said inner conducting wall of the capsule and said needle, the improvement comprising:
   an AC generator the input of which is connected to the positive pole of a DC source,
   an assembly including a rectifier and filter, said assembly being connected
     by a first input terminal to the output of said generator,
     by a second terminal to the negative pole of said source,
   at least one comparator connected
     by lead-out to said signaling device,
     by lead-in to a third output terminal of the rectifier/filter assembly and to a comparison unit intended to provide a reference voltage, said comparator being subjected to the difference in voltage between that delivered by said rectifier/filter assembly and that delivered by said comparison unit and being fed, with said signaling device, by said DC source,
   a surface electrode placed on a patient's skin, said electrode being connected to the negative pole of the source and, in the circuit's closed state, in series with said needle, the patient's body, and/or said inner wall of the capsule, towards the input terminal of said rectifier/filter assembly.

2. The system according to claim 1, wherein the rectifier/filter assembly further includes:
   a current-rectifying component such as a diode placed on the feed line joining the input terminal and the output terminal of the assembly,
   a condenser connected both to said feed line at the site of the cathode of said diode and to the negative pole of the source, and
   a resistor mounted parallel to the terminals of said condenser.

3. A system according to claim 1 wherein said comparison unit includes:
   a sequencing clock, one input terminal of which is connected to the output terminal of said rectifier/filter assembly,
   two switches each placed under the control of said clock and connected to one another at one of their transient terminals,
     said first switch, through its other transient terminal, being connected to one of the terminals of a voltage dividing bridge, itself linked to the output terminal of said rectifier/filter assembly, the other terminal of the dividing bridge being connected to the negative pole of the source, and
     said second switch being connected, also through its other transient terminal, to a lead-in of the comparator, the clock and the two switches,
   a condenser connected on one side to the negative pole of said source and on the other at the site of a linkage between the two switches.

4. A system according to claim 3, further including two comparators,
   the first being connected by its two lead-ins respectively to the output terminal of said rectifier/filter assembly and to said other transient terminal of the second switch, the lead-out of this first comparator being directly linked to said signaling device,
   the second comparator being placed between the output terminal of said rectifier/filter assembly and the input terminal of said clock, the comparison unit to which is connected one of the lead-ins of this second comparator being of the type delivering a determined, fixed voltage.

5. A system according to claim 4, further comprising two voltage followers each placed between the output terminal of said rectifier/filter assembly and the corresponding lead-in of the comparator which is subjected to the voltage difference between that delivered by said rectifier/filter assembly and that delivered by said comparison unit, both followers being fed by said DC source.

6. A system according to claim 1, wherein said capsule is formed by a conducting metal wall forming the bottom of the capsule, on which is molded the remainder of the capsule in non-conducting plastic, including the tight, perforatable partition opposite the bottom wall.

7. A system according to claim 6, wherein the capsule's metal bottom is formed by a part shaped by stamping, having the shape of a basin closable on its upper part by the perforatable partition forming the cover.

8. A system according to claim 6, including a metal adapter attached to said metal bottom connecting the inside of the capsule to the implanted dispensing tube.

* * * * *

UNITED STATES PATENT AND TRADEMARK OFFICE
CERTIFICATE OF CORRECTION

PATENT NO. : 4,781,685
DATED : November 1, 1988
INVENTOR(S) : Gerard Lehmann, et al.

It is certified that error appears in the above-identified patent and that said Letters Patent is hereby corrected as shown below:

Column 4, line 9, change "assembly" to --switch--.

Column 4, line 10, change "switch" to --assembly--.

Column 5, line 15, change "$\bar{\rho}$" to --$\rho$--.

Column 5, line 19, change "$\rho$" to --$\bar{\rho}$--.

Column 5, line 39, change "v" to --$\underline{v}$--.

Column 5, line 40, change "v" to --$\underline{v}$--.

Column 6, line 34, delete "about" (second occurrence).

Signed and Sealed this

Twentieth Day of June, 1989

Attest:

DONALD J. QUIGG

*Attesting Officer*     *Commissioner of Patents and Trademarks*

UNITED STATES PATENT AND TRADEMARK OFFICE
CERTIFICATE OF CORRECTION

PATENT NO. : 4,781,685

DATED : November 1, 1988

INVENTOR(S) : Gerard Lehmann, et al.

It is certified that error appears in the above-identified patent and that said Letters Patent is hereby corrected as shown below:

Column 8, line 22, after "switches" insert --being in addition fed with direct current by said source--.

Signed and Sealed this

Fourteenth Day of November, 1989

Attest:

JEFFREY M. SAMUELS

Attesting Officer    Acting Commissioner of Patents and Trademarks